United States Patent [19]

Gehrke

[11] Patent Number: 4,553,094

[45] Date of Patent: Nov. 12, 1985

[54] METHOD AND APPARATUS FOR MEASURING CONDUCTIVITY USING EDDY CURRENTS WITH TEMPERATURE COMPENSATION FEATURE

[75] Inventor: Robert E. Gehrke, Wixom, Mich.

[73] Assignee: K. J. Law Engineers, Inc., Farmington Hills, Mich.

[21] Appl. No.: 505,881

[22] Filed: Jun. 20, 1983

[51] Int. Cl.⁴ .................. G01R 33/12; G01N 27/72
[52] U.S. Cl. .................................. 324/225; 324/233; 324/243
[58] Field of Search ......... 324/233, 224, 225, 239–243

[56] References Cited

U.S. PATENT DOCUMENTS

| | | | |
|---|---|---|---|
| 3,525,931 | 8/1970 | Aisenberg | 324/224 X |
| 3,651,398 | 3/1972 | Urmenyi | 324/224 |
| 4,095,180 | 6/1978 | Brown | 324/233 |

Primary Examiner—Gerard R. Strecker

Attorney, Agent, or Firm—Barnes, Kisselle, Raisch, Choate, Whittemore & Hulbert

[57] ABSTRACT

Method and apparatus for measuring conductivity of test materials at a measurement temperature and displaying material conductivity at standard temperature by compensating the measured conductivity for conductivity changes due to the measurement-standard temperature differential. This is accomplished by developing a first periodic signal having a period which varies as a direct linear function of material conductivity $C_T$ at the measurement temperature, and a second periodic signal having a period which varies as a function of the product of measured conductivity $C_T$, the measurement/standard temperature differential $\Delta T$ and a conductivity constant $\beta$ characteristic of non-ferrous metals having a given base metal. Standard conductivity $C_S$ is then determined in accordance with the equation $C_S = C_T (1 + \beta C_T \Delta T)$ as a combined function of the periods of the first and second signals, and is displayed in percent IACS at 20° C.

17 Claims, 3 Drawing Figures

METHOD AND APPARATUS FOR MEASURING CONDUCTIVITY USING EDDY CURRENTS WITH TEMPERATURE COMPENSATION FEATURE

The present invention relates to conductivity test equipment and methods, and more particularly to a method and apparatus for measuring the conductivity of non-ferrous metals using electromagnetic induction or eddy current principles. Yet more specifically, the invention relates to improvements for purposes of temperature compensation to the method and apparatus disclosed in U.S. Pat. No. 4,095,180.

U.S. Pat. No. 4,095,180, assigned to the assignee hereof, discloses a method and apparatus for measuring conductivity of non-ferrous metals employing eddy current principles. Conductivity is measured as a direct linear function of the period of the eddy current-inducing signal at a preselected phase angle between the inducing and induced eddy current signals, and is displayed directly in percentage of International Annealed Copper Standard (percent IACS). The method and apparatus so disclosed solve many problems previously extant in the art and provide a reliable measurement of actual conductivity at the actual measurement temperature.

Material conductivity is often used as a quality control check on composition of non-ferrous metal alloys. It may be specified, for example, that a particular alloy has a given conductivity in percent IACS at 20° C., which is the standard temperature for conductivity specifications. However, it is seldom convenient to perform the actual measurement at 20° C. Charts, nomographs or other similar devices may be employed to relate measured conductivity to standard conductivity, requiring of course that measurement temperature be known and material composition be assumed since required temperature compensation differs with material. Another prior art technique contemplates measurement of an unknown sample and interpolative comparisons to measured conductivity for two or more standard specimens. However, the mathematics of compensation vary non-linearly with standard conductivity (at 20° C.) within a given class of alloys having a common base metal, so that, unless the standard specimens are close to the unknown sample, this technique, which assumes linearity, results in significant error.

It is therefore an object of the present invention to provide an improved apparatus and method for measuring conductivity of non-ferrous metals while compensating such measurement for the effects of temperature.

More specifically, it is an object of the invention to provide a method and apparatus of the described character which measure and directly display conductivity in percent IACS at standard temperature, specifically 20° C., regardless of the temperature at which the measurement is performed.

Another and yet more specific object of the invention is to provide a method and means for compensating the conductivity measurement obtained in accordance with the teachings of U.S. Pat. No. 4,095,180 for conductivity changes in the test material due to variations in temperature from the IACS standard temperature (20° C.).

The invention, together with additional objects, features and advantages thereof, will be best understood from the following description, the appended claims and the accompanying drawings in which:

Figure 1:
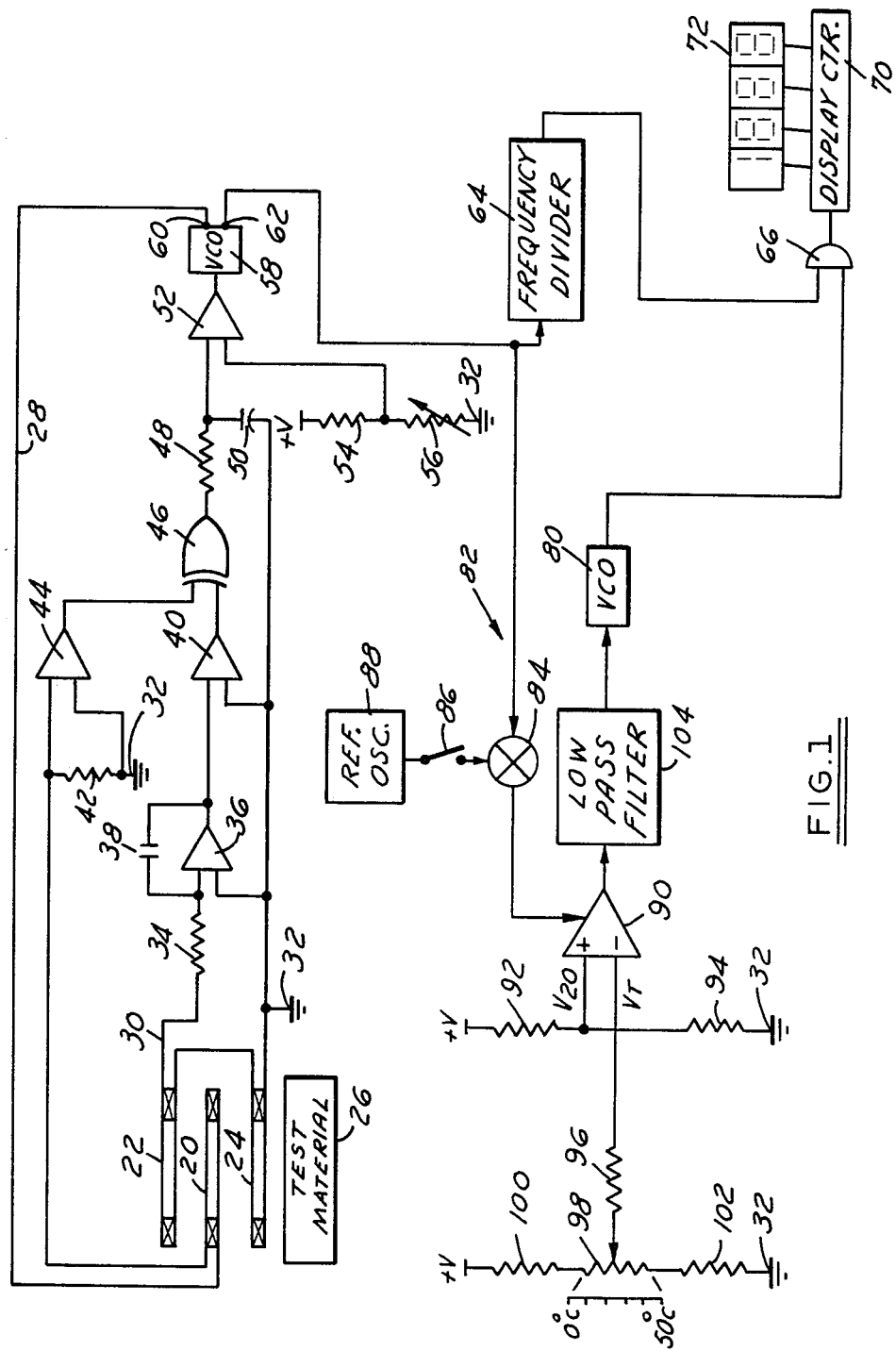
FIG. 1 is a schematic diagram of a presently preferred embodiment of an eddy current conductivity meter in accordance with the invention.

Referring to FIG. 1, a primary coil 20 and a pair of secondary coils 22,24 are disposed as shown in close proximity to a test material 26. Primary coil 20 receives a periodic inducing current signal via conductor 28 and, in accordance with well-known theory, eddy currents are induced in material 26 as a function, among other properties, of the material conductivity. Secondary coils 22,24 are so disposed with respect to coil 20 and are connected to each other in a manner as to produce between secondary coil output line 30 and common bus or circuit ground 32 a differential voltage signal which varies as a function of the electromagnetic field generated by eddy currents in material 26 but independently of any direct coupling between the primary coil 20 and the secondary coils 22,24.

The induced signal on line 30 is fed to an integrator comprising a resistor 34, an amplifier 36 and a capacitor 38 to develop an output which varies as an integral function of the induced voltage signal on line 30. The output of integrating amplifier 36 is fed to a switching amplifier 40 which provides at its output a square wave signal at the frequency of the induced voltage signal in coils 22,24 and lagging ninety degrees with respect thereto. Coil 20 is connected through a resistor 42 to ground 32 to convert the inducing current signal to a voltage, which is applied to the input of a switching amplifier 44 whose output is a square wave signal at the frequency and phase angle of the inducing signal in coil 20.

The outputs of switching amplifiers 40,44 are connected to respective inputs of a phase detector comprising an exclusive-OR (EOR) gate 46 which has its output serially connnected through a resistor 48 and a capacitor 50 to ground 32. The output of gate 46 is low or a logical zero when the respective outputs of amplifiers 40,44 are the same (low or high) and is high or a logical one when the respective outputs of amplifiers 40,44 are different. Resistor 48 and capacitor 50 act as a low pass filter to provide across the capacitor a dc analog signal whose amplitude is proportional to the duty cycle of the output of gate 46, and hence proportional to the phase angle relationship between the induced and inducing signals represented by the outputs of amplifiers 40,44 respectively. The phase relationship signal across capacitor 50 is fed to one input of an error amplifier 52 which receives its second or reference input from the center junction of a resistor voltage divider 54,56 connected between a +V voltage source and ground 32. Resistor 56 is made adjustable for factory setting of the reference input to amplifier 52 to a preselected level representative of a preselected phase relationship between the induced and inducing signals.

The output of amplifier 52, which is indicative of the difference between the measured and desired phase relationship between the induced and inducing signals, is fed to a voltage-controlled oscillator 58 which provides buffered outputs 60,62 as a function of the control signal from amplifier 52. Although the periodic output at 60,62 may be a sinusoidal signal, it has been found that a periodic triangular or zigzag output signal may be generated less expensively than a pure sinusoidal signal and may be used without any noted detrimental effect upon instrument accuracy. Output 60 is fed via conductor 28 to primary coil 20.

Oscillator output 62 is fed to a frequency divider 64 which (1) divides the oscillator output by a selected scaling factor to reduce the effect of noise and jitter on the output display, and (2) then divides the scaled frequency by two to provide a signal indicative of the period of the scaled frequency. Stated differently, frequency divider 64 comprises a first frequency divider to reduce the frequency of oscillator output 62 by a selected scaling factor, and a second frequency divider to divide the output of the first divider by two and to thus yield a signal indicative of the period of the first divider output; i.e., high during the first period of the first divider output, low during the second period, high during the third period, etc. The output of frequency divider 64 is fed to one input of an AND gate 66 which receives a second input from a voltage controlled oscillator 80 which forms part of the temperature compensation circuit 82 in accordance with the present invention. Thus, the output of gate 66 comprises the output of oscillator 80 gated by the output of frequency divider 64 and provides a measure or count of the period of oscillator output 62 divided by the scaling factor. The output of gate 66 is connected to a display counter 70 and associated seven-segment display 72 to provide a digital readout as a function of measured period.

Operation of the circuit of FIG. 1 to the extent thus far described, without compensation circuit 82 and with a fixed frequency reference oscillator in place of voltage controlled oscillator 80, is described in detail in U.S. Pat. No. 4,095,180, the entirety of which is incorporated herein by reference. In general, conductivity of test piece 26 is measured as a direct linear function of the period of the inducing signal output of oscillator 58 at a predetermined phase relationship between the inducing and induced signals. This phase relationship is measured by EOR gate 46, and the frequency (and period) of the inducing signal is varied by amplifier 52 and VCO 58 until this phase relationship is at the level set by resistor 56. The period of the inducing signal is then measured by divider 64, gate 66 and oscillator 80, and the result is displayed at 70,72 as a direct scaled function in percent IACS. For a more detailed description of operation, as well as the manner of selecting such parameters as phase angle and signal frequency, etc., resort may be had to the above-referenced patent disclosure.

In temperature compensation circuit 82 provided in accordance with the invention, output 62 of oscillator 58 is fed to one input of a mixer 84. The second input of mixer 84 is connected by a switch 86 to a fixed frequency reference oscillator 88. Switch 86 is provided for operator selection of normal or uncompensated operation (switch open) and temperature-compensated operation (switch closed). The output of mixer 84 is connected to the control input of a gated comparator 90. The non-inverting input of comparator 90 is connected to the junction of the voltage divider resistors 92,94 which are connected in series across the +V dc power supply. The values of resistors 92,94 are selected to provide a fixed reference voltage $V_{20}$ to comparator 90, taken as representative of the IACS standard temperature of 20° C.

The inverting input of comparator 90 is connected through a resistor 96 to the wiper of a variable resistor 98. Resistor 98 is connected in series with the resistors 100,102 across the +V dc supply. The wiper of variable resistor 98 is positionable by an operator (through means not shown) as a function of measurement temperature. Thus, the voltage $V_T$ supplied by resistor 96 to comparator 90 varies with measurement temperature, and the voltage differential $V_{20} - V_T$ across the inputs of comparator 90 is indicative of the difference between measurement temperature and IACS standard temperature 20° C. When resistor 98 is set at a position corresponding to 20° C., this voltage differential is zero. The values of resistors 96–102 are selected in comparison with resistors 92,94 to provide a useable voltage differential at the comparator inputs over the expected temperature operating range of the instrument. The output of comparator 90, which is a periodic pulsed signal having a pulse duration and frequency controlled by mixer 84 and an amplitude which is a function of the temperature differential described above, is fed through a low pass filter 104 to the control input of VCO 80.

Figure 2:
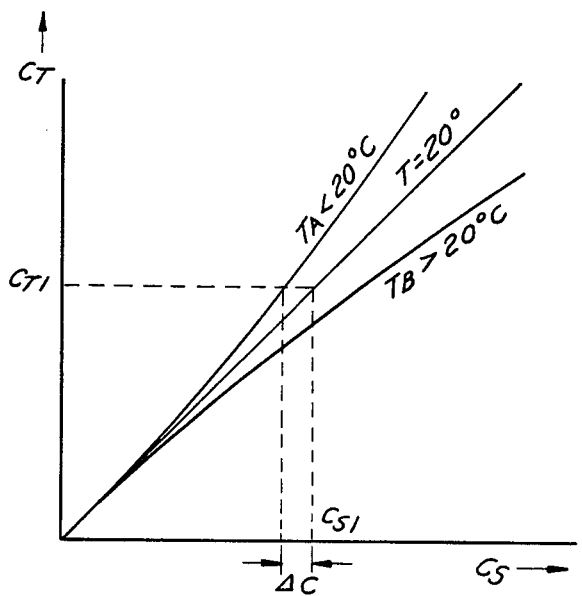
FIG. 2 is a graphic illustration useful in understanding operation of the invention.

Before describing operation of temperature compensation circuit 82 in detail, reference is made to FIG. 2 for a discussion of theoretical background. FIG. 2 is a graphic illustration (not to scale) of the difference or error between actual material conductivity $C_T$ and so-called standard conductivity $C_S$ for different alloys as the measurement temperature T departs from 20° C. at which the standard conductivity is obtained or calibrated. Where measurements are performed at 20° C., actual conductivity $C_T$ will, of course, equal standard conductivity $C_S$ for the material under test. However, as the temperature departs from the standard of 20° C., compensation is required in order to relate actual conductivity to standard conductivity—i.e. percent IACS at 20° C. Thus, for example, a measurement performed at a temperature $T_A$ less than 20° C. on a given test material 26 having an actual conductivity $C_{T1}$ at that temperature requires compensation $\Delta C$ to yield the desired 20° C. standard conductivity $C_{S1}$ for that test piece.

As is well-known in the art, actual conductivity $C_T$ at temperature T is related to the so-called standard conductivity $C_S$ at 20° C. by the equation:

$$C_T = C_S(1 + \alpha \Delta T) \tag{1}$$

where $\alpha$ is a temperature coefficient or correction factor and $\Delta T$ is departure of measurement temperature from 20° C. For a given material or alloy, $$\alpha = \beta C_S \tag{2}$$

where $C_S$ is standard conductivity at 20° C. for that material or alloy and $\beta$ is a constant. In fact, $\beta$ is a constant for any given class of alloys having the same base metal. Combining (1) and (2):

$$C_T = C_S + \beta C_S^2 \Delta T. \tag{3}$$

Hence, the non-linear curves in FIG. 2 for temperature ($T_A$ and $T_B$) other than 20° C.

In the present invention, the actual conductivity $C_T$ is, of course, the starting point, and it is desired to obtain standard conductivity for the material under test. From (1) and (2):

$$\begin{aligned} C_S &= C_T(1 - \beta C_S \Delta T) \\ &= C_T - \beta C_T C_S \Delta T \end{aligned} \tag{4}$$

In the operation of the circuit of FIG. 1 to be described, actual conductivity $C_T$ is used in place of standard conductivity $C_S$ in the quantity $\beta C_T C_S \Delta T$, resulting in negligable error. Thus $$C_S = C_T(1 - \beta C_T \Delta T) \tag{5}$$

Turning now to operation of compensation circuit 82 (FIG. 1), the frequency of oscillator 88 is selected as a function of $\beta$ for the type of alloy for which the instrument is designed. For aluminum alloys for example, $\beta$ is equal to about $66 \times 10^{-6}$, and using appropriate scaling based on circuit parameters such as VCO sensitivity 80, etc., a frequency of 3.39KHz at oscillator 88 is appropriate. The input to mixer 84 from oscillator 58 is, of course, indicative of measured conductivity $C_T$, and the output of mixer 84 is thus a function of the product $\beta C_T$. This output operates in gated comparator 90 to pulse-width modulate or multiplex the temperature differential comparator input $V_{20} - V_T$, so that the pulsed output is indicative of the product $\beta C_T \Delta T$ in equation (5). That is, the duration of the pulsed output of comparator 90 is indicative of $\beta C_T$, and the amplitude is indicative of $\Delta T$. Low pass filter 104 effectively integrates this pulsed signal so as to provide a d.c. control signal to VCO 80 as a function of the product $\beta C_T \Delta T$. Voltage controlled oscillator 80 thus operates through gate 66 to clock display counter 70 as a function of the quantity $(1 - \beta C_T \Delta T)$ in equation (5).

The unit of FIG. 1 is initially calibrated by opening switch 86 and calibrating by factory adjustment of resistor 56 as described in the above-referenced patent. Thereafter, the unit may be operated in the "uncompensated" mode by leaving switch 86 open, so that VCO 80 operates at its nominal frequency and operation proceeds as described in the referenced patent. For temperature-compensated operation, switch 86 is closed and operation proceeds as described immediately above. It will be appreciated that oscillator 88 may be made operator-variable to accommodate differing base metals, and therefore different $\beta$'s. It is presently preferred, however, to calibrate oscillator 88 at the factory for a specific base metal.

Gate 66 is where the quadratic solution to equation (5) actually takes place. Just as conductivity is measured as a direct linear function of the period of the eddy current inducing signal, the conductivity offset $\Delta C$, which depends on temperature and conductivity, adds to or subtracts from the digital reading. When $\Delta T = O$ ($T = 20°$ C.), $\Delta C$ also is zero, and an uncompensated reading results. FIG. 2 illustrates the $\Delta C$ offset which is required.

When T is about 20° C., $\Delta C$ will offset the lower reading that would normally result from the lowered conductivity. Required compensation $\Delta C$ is produced digitally from true conductivity and adds or subtracts appropriately to give a standard readout of conductivity when measurement temperature is set at resistor 98. Alternately, when the 20° C. conductivity of a standard specimen is known, the setting of resistor 98 will then indicate measurement temperature. Of course, this useful feature will be accurate over a wide conductivity range but only for the alloy type used as the standard. For example, any aluminum alloy may be used as a standard to determine the value of another aluminum standard. However, a differential metal will read accurately only if an alloy of that metal is used in the compensation step.

Temperature compensation as described above has been determined by manually setting temperature T on calibrated variable resistor 98. By appropriate substitution of a suitable thermistor mounted in the eddy current probe near the test material 26, this step can be eliminated. Fully automatic compensation is accomplished by substitution of the network shown in FIG. 3, or any other sensor designed to maintain the linear $V_T/T$ relationship supplied at resistor 96. Therefore, reading errors caused by part warming or cooling are continuously corrected, or this input may be used as part of a process control loop using conductivity measurement.

Figure 3:
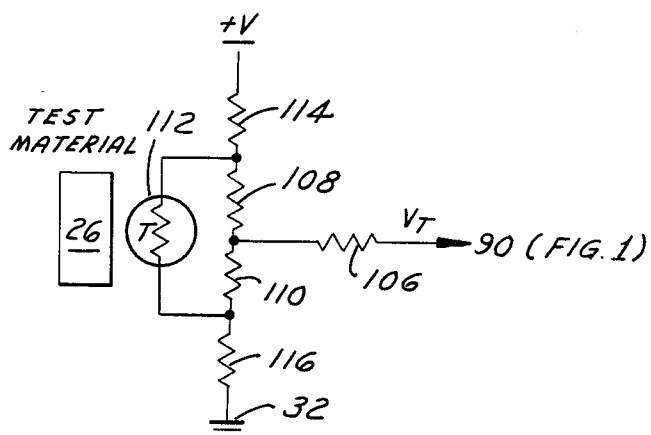
FIG. 3 diagrams a fragmentary modification necessary for automating the temperature compensation process.

More particularly, as shown in FIG. 3, the thermistor 112, which may be mounted in the test probe so as to be disposed adjacent to test material 26, is connected across the series-connected resistors 108,110. Resistors 108,110 are connected to the $+V$ voltage source and to ground 32 by the resistors 114,116 respectively. The junction of resistors 108,110 is connected through a resistor 106 to supply the variable temperature voltage $V_T$ to the inverting input of amplifier 90 in FIG. 1.

It has been found that the temperature compensation technique described above results in improved accuracy on the order of 0.5% IACS. Temperature errors in computing $\Delta C$ by methods other than as described above, or which do not use conductivity in the computation, would not obtain this type of accuracy figure. It is especially useful here that normal calibration of the loop is not distributed by the compensation process, so that true conductivity is always available from the period of the eddy current signal. This same period also pulse-width modulates the input temperature offset over a practical temperature range from 0% to 50° C. Therefore, it is clear that, unlike other methods which ignore temperature effects or lump then into response-correcting circuits, the present invention measures true conductivity $C_T$ as a directlinear function of the period of the loop frequency, and temperature-compensates measured conductivity to display the corresponding standard conductivity $C_S$ in percent IACS at standard temperature, specifically 20° C., regardless of the temperature at which the measurement is performed.

A particular test piece can be read in both normal and compensated modes, with the latter measurement compensating automatically for $\alpha \Delta T$. Where these readings differ, the expected $\alpha$ was not obtained. This means that $\beta C_T$ differs from $\beta C_S$, implying that some condition in the sample's history, such as tempering, ageing or stressing, has altered the conductivity $C_T$. This is because a small difference $(C_T - C_S)$ produces only a minor error in $\Delta C$. The degree of difference in readings between normal and compensated modes may indicate the type or degree of past changes, or the condition of the metal's crystal lattice. This structural form determines the $\beta$ coefficient and permits tabulation or historical changes such as this. Such tabulation normally requires difficult and time consuming analysis, also being subject to significant error. Furthermore, while it is known that $\beta$ remains constant through most of a metal's alloying range, any degree of minor deviation from this rule can now be gauged.

The invention claimed is:

1. Apparatus for determining conductivity at a preselected standard temperature of test alloy materials having a predetermined nonferrous base metal by measuring conductivity at a measurement temperature comprising first means for inducing eddy currents in a said test material and providing a first signal having a period which varies as a function of conductivity of the test material, second means for providing a second signal having a period which varies as a function of a difference between measurement temperature and said preselected temperature including means for providing a third signal as a function of a conductivity constant which is characteristic of said base metal, means for providing a fourth signal as a function of the product of said first signal, said third signal and said temperature difference, and means for varying said period of said second signal as a function of said fourth signal, and third means for determining conductivity of the test material as a combined function of the periods of said first and second signals.

2. The apparatus set forth in claim 1 wherein said means for providing said third signal comprises first oscillator means having an output frequency determined by said constant.

3. The apparatus set forth in claim 2 wherein said means for providing said fourth signal comprises mixer means having inputs responsive to said first signal and to said first oscillator means, and gated amplifier means having differential inputs responsive to said measurement temperature and to said standard temperature and a gate input responsive to said mixer means.

4. The apparatus set forth in claim 3 further comprising temperature-responsive resistance means connected to said gated amplifier means and adapted to be so disposed with respect to the test material as to be automatically responsive to the temperature thereof.

5. The apparatus set forth in claim 3 wherein said second means comprises second oscillator means coupled to said gated amplifier means for varying said period of said second signal as a function of the output of said gated amplifier means.

6. The apparatus set forth in claim 1 wherein said third means comprises a frequency divider for dividing the frequency of said first signal by twice a preselected scaling factor, a counter and means gating said second signal to said counter during half-cycles of said frequency-divided signal, such that the count in said counter after a said half-cycle is equal to said scaling factor multiplied by the ratio of the period of said first signal divided by the period of said second signal.

7. The apparatus set forth in claim 6 further comprising digital display means for displaying said count after each said half-cycle.

8. The apparatus set forth in claim 7 wherein said display means and said second means are calibrated to display conductivity in percent IACS at a standard temperature of 20° C.

9. Apparatus for determining conductivity at a preselected standard temperature of non-ferrous test materials comprising means for inducing eddy currents in a said test material at a measurement temperature and developing a first signal having a period which varies as a direct linear function of conductivity of the test material at said measurement temperature, means for setting said measurement temperature to develop a second signal as a function of a difference between said measurement temperature and said standard temperature, means responsive to said second signal for providing a third signal having a period which varies as a linear function of said temperature difference, counter means responsive to said first and third signals for counting occurrences of said third signal during one period of said first signal, and means for developing said conductivity at standard temperature as a function of the count in said counter means after said one period of said first signal.

10. The apparatus set forth in claim 9 wherein said means for setting said measurement temperature comprises means adapted to be disposed adjacent to the test material so as to be automatically responsive to the temperature thereof.

11. The apparatus set forth in claim 10 wherein said means for inducing eddy currents in a test material comprises a probe containing multiple signal coils, and wherein said temperature-responsive means comprises temperature-responsive resistance means disposed in said probe.

12. A method of measuring conductivity of a non-ferrous test piece having a predetermined base metal at a measurement temperature and displaying measured conductivity as a value compensated to reflect conductivity of the test piece at a predetermined standard temperature different from said measurement temperature, said method comprising the steps of:

(a) providing a first periodic signal in proximity to a test piece to induce eddy currents therein as a function of conductivity of the test piece at said measurement temperature, (b) developing a test signal which varies as a function of said eddy currents, (c) varying the frequency of said first periodic signal until said first periodic signal is at a predetermined phase relationship with respect to said test signal, (d) providing a second periodic signal having a period which varies as a function of the difference between said measurement temperature and said standard temperature by (d1) providing a third signal which varies as a function of the product of said temperature difference, said period of said first periodic signal and a conductivity constant characteristics of said base metal, and (d2) varying the period of said second periodic signal as a function of said product, (e) determining conductivity of the test piece at said standard temperature as a function of the periods of said first and second periodic signals, and (f) displaying conductivity at said standard temperature determined in said step (e).

13. In the method of measuring conductivity of materials which includes the steps of providing a first periodic signal in proximity to a conductive test piece to induce eddy currents therein, developing a test signal which varies as a function of said eddy currents, varying the frequency of said first periodic signal to a frequency at which said first periodic signal is at a predetermined phase relationship to said test signal, and measuring conductivity of said test piece as a direct linear function of the period of said firt periodic signal at said predetermined phase relationship by providing a second periodic signal and counting periods of said second periodic signal as a function of the period of said first periodic signal, the improvement for compensating said measured conductivity for effects due to temperature comprising the step of scaling measured conductivity to conductivity at a preselected standard temperature by determining measurement temperature at which said step of measuring conductivity is performed and then controlling frequency of said second periodic signal as a function of a different between said measurement temperature and said standard temperature, said step of measuring conductivity comprising the step of dividing said frequency of said first periodic signal by twice a preselected scaling factor to provide a scaled output signal and counting periods of said second periodic signal during a half-cycle of said scaled output signal.

14. Apparatus for determining conductivity of test alloy materials having a preselected non-ferrous base metal comprising means for inducing eddy currents in a test material at a measurement temperature and developing a first signal which varies as a function of conductivity of the test material at said measurement temperature, means for developing a second signal which varies as a function of said measurement temperature, means for providing a third signal as a function of a predetermined conductivity characteristic of the test material, means for providing a fourth signal as a function of the product of said first, second and third signals, and means for determining conductivity of the test material as a combined function of said first and said fourth signals.

15. The apparatus set forth in claim 14 for determining conductivity of test materials at a preselected standard temperature wherein said means for developing said second signal includes means for providing said second signal as a function of a difference between said measurement temperature and said preselected standard temperature.

16. The apparatus set forth in claim 15 wherein means for determining conductivity comprises means for determining conductivity at said standard temperature as a function of the sum of said first signal plus the product of said first signal times said fourth signal.

17. The apparatus set forth in claim 16 wherein said first signal varies as a direct linear function of conductivity at said measurement temperature.

* * * * *